US00PP22195P2

(12) United States Plant Patent
Prebble et al.

(10) Patent No.: US PP22,195 P2
(45) Date of Patent: Oct. 11, 2011

(54) ***ASTELIA* PLANT NAMED 'SILVER SHADOW'**

(50) Latin Name: ***Astelia chathamica*×*Astelia nervosa***
Varietal Denomination: Silver Shadow

(76) Inventors: Tim Prebble, Churchchrist City (NZ); Hamish Prebble, Churchchrist City (NZ)

( * ) Notice: Subject to any disclaimer, the term of this patent is extended or adjusted under 35 U.S.C. 154(b) by 0 days.

(21) Appl. No.: 12/806,648

(22) Filed: Aug. 18, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Annette Para
(74) *Attorney, Agent, or Firm* — Penny J. Aguirre

(57) ABSTRACT

A new cultivar of *Astelia* named 'Silver Shadow' that is characterized by its foliage that is green in color with a silver overlay on the upper and lower leaf surface, its small leaves, and its dwarf, broad, and mounded plant habit.

2 Drawing Sheets

Botanical classification: *Astelia chathamica*×*Astelia nervosa.*

Cultivar designation: 'Silver Shadow'.

BACKGROUND OF THE INVENTION

The present invention relates to a new and distinct cultivar of *Astelia* named 'Silver Shadow', an interspecific hybrid of *Astelia chathamica*×*Astelia nervosa* and referred to hereafter by its cultivar name, 'Silver Shadow'. The new cultivar is grown for use as a foliage plant for landscape and container use.

'Silver Shadow' was selected in the Inventors' greenhouse in December 2004 as a single unique plant from amongst the seedlings derived from a cross made in November 2003 between an unnamed plant of *Astelia chathamica* as the female parent and an unnamed plant of *Astelia nervosa* as the male parent.

Asexual reproduction of the new cultivar was first accomplished by division in March of 2005 in Christchurch City, New Zealand by one of the Inventors. Asexual reproduction by division and tissue culture has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Silver Shadow' as a new and unique cultivar of *Astelia.*

1. 'Silver Shadow' exhibits foliage that is green in color with a silver overlay on the upper and lower leaf surface.
2. 'Silver Shadow' exhibits leaves that are small in size.
3. 'Silver Shadow' exhibits a dwarf, broad, and mounded plant habit.

'Silver Shadow' can be compared to its parent plants. The female parent, *Astelia chathamica*, differs from 'Silver Shadow' in having larger leaves that have a silver overlay only on the lower surface and in having a larger plant size. The male parent, *Astelia nervosa* differs from 'Silver Shadow' in having leaves that have a silver overlay only on the upper surface and in having narrower leaves and a smaller plant size. The closest comparison cultivar is 'Silver Spear' (not patented), which is similar in having leaves with a silver overlay. The foliage of 'Silver Spear' differs from 'Silver Shadow' in having leaves that more silver, in having an upright plant habit, and in being more frost resistant.

BRIEF DESCRIPTION OF THE DRAWING

The accompanying colored photographs illustrate the overall appearance and distinct characteristics of the new *Astelia*. The photographs in FIG. 1 and FIG. 2 were taken of a six month-old plant of 'Silver Shadow' as grown in a greenhouse in a 10-cm container in Stoneyford, Republic of Ireland.

DETAILED BOTANICAL DESCRIPTION OF THE PLANT

Figure 1:
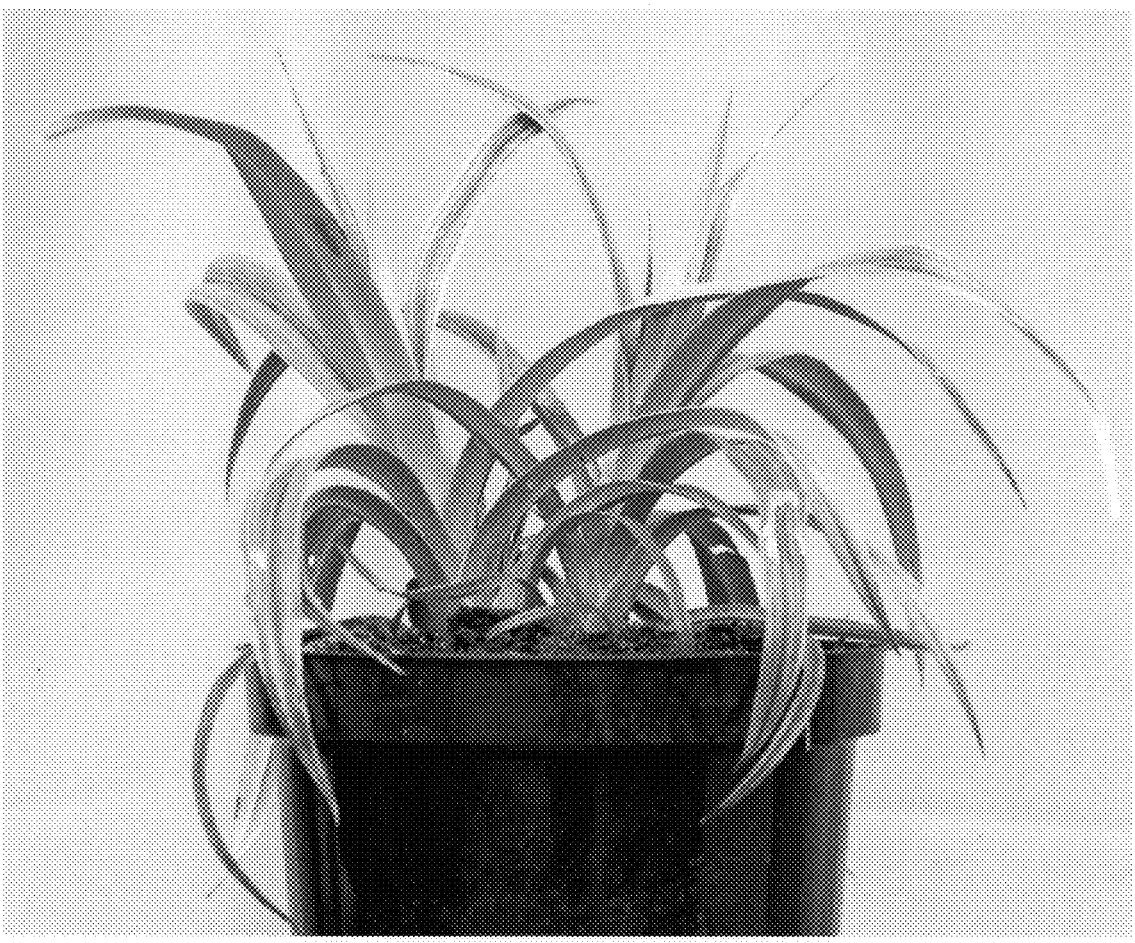
FIG. 1 provides a side view of 'Silver Shadow'.
Figure 2:
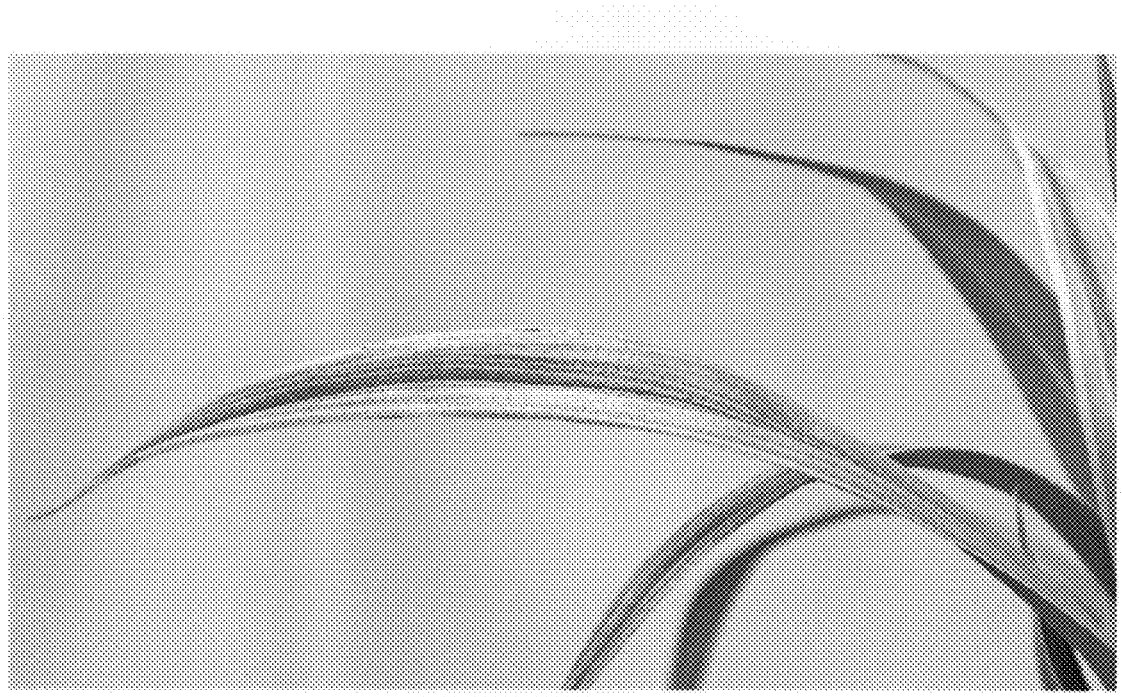
FIG. 2 provides a close up view of the foliage of 'Silver Shadow'. The colors in the photographs may differ slightly from the color values cited in the detailed botanical description, which accurately describe the colors of the new *Astelia.*

The following is a detailed description of six month-old plants of 'Silver Shadow' as grown in a greenhouse in 10-cm containers in Stoneyford, Republic of Ireland. The plants were grown under normal light levels with average day temperatures of 12° to 22° C. and average night temperatures of 8° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General Description:

*Blooming period.*—No flower production has been observed.

*Plant type.*—Herbaceous perennial.

*Plant habit.*—Dwarf, broad-mounded, with arching leaves.

*Height and spread.*—Reaches an average of 22 cm in height and 39 cm in width.

*Hardiness.*—Observed to be tolerant to high temperatures of 40° C. and low temperatures of −5° C.

*Diseases and pests.*—No unique susceptibility or resistance to diseases or pests has been observed.

*Root description.*—Fibrous, dense, moderately branched, 155A in color.

*Propagation.*—Division and tissue culture (preferred).

*Growth rate.*—Moderate.

*Root development.*—4 to 5 weeks to initiate roots on a tissue culture propagule, about 3 months to fully develop new roots on a young plant when grown at night temperatures of 7° C. night and day temperatures of 15° C.

*Stem description.*—Stem-less, leaves are equitant from base.

Foliage description:

*Leaf shape.*—Ensiform.

*Leaf division.*—Simple.

*Leaf base.*—Decurrent.

*Leaf apex.*—Long acuminate.

*Leaf venation.*—Parallel, not prominent, same color as leaves, mid rib protruding on lower surface.

*Leaf margins.*—Entire with short sericeous hairs.

*Leaf attachment.*—Sheathed to base.

*Leaf arrangement.*—Equitant.

*Leaf number.*—Average of 15 per shoot, 2 shoots (tufts) per 10-cm container.

*Leaf orientation.*—Initially upright and becomes arching.

*Leaf substance.*—Thick, durable.

*Leaf surface.*—Upper and lower surface: glossy and densely pubescent with sericeous hairs; an average of 1 mm in length and NN155d in color, hairs are almost not discernable as individual hairs, hairs on margin are an average of 1.5 mm in length.

*Leaf color.*—Young leaves upper and lower surface; 144A to 144B with a pubescent surface with the effect of N155A in areas of coverage, mature leaves upper surface; 137B to 137C with a pubescent surface with the effect of N155A in areas of coverage, mature leaves lower surface; 137B with base of leaves 144C to 144D with a pubescent surface with the effect of N155A in areas of coverage.

*Leaf size.*—An average of 23.5 cm in length and 2.3 cm in width.

Flower description: The new *Astelia* is grown as a foliage plant and has not been observed to produce flowers.

It is claimed:

1. A new and distinct cultivar of *Astelia* plant named 'Silver Shadow' as herein illustrated and described.

* * * * *